United States Patent
Schütz

(10) Patent No.: US 7,621,766 B2
(45) Date of Patent: Nov. 24, 2009

(54) ELECTRIC PLUG DEVICE INCLUDING INTEGRATED HYDRAULIC/PNEUMATIC PORTS

(75) Inventor: Günter Schütz, Meitingen (DE)

(73) Assignee: Invendo Medical GmbH, Weinheim (DE)

( * ) Notice: Subject to any disclaimer, the term of this patent is extended or adjusted under 35 U.S.C. 154(b) by 0 days.

(21) Appl. No.: 12/035,176

(22) Filed: Feb. 21, 2008

(65) Prior Publication Data

US 2008/0207028 A1 Aug. 28, 2008

(30) Foreign Application Priority Data

Feb. 22, 2007 (DE) ........................ 10 2007 000 109

(51) Int. Cl.
*H01R 4/60* (2006.01)
(52) U.S. Cl. ..................................................... 439/191
(58) Field of Classification Search .................. 439/191, 439/372, 198
See application file for complete search history.

(56) References Cited

U.S. PATENT DOCUMENTS

| 4,525,918 | A | | 7/1985 | Puritz |
| 4,576,144 | A | | 3/1986 | Ishii |
| 4,708,126 | A | | 11/1987 | Toda et al. |
| 4,720,128 | A | | 1/1988 | Logan, Jr. et al. |
| 5,017,136 | A | * | 5/1991 | Gatti ............................ 433/98 |
| 5,405,269 | A | * | 4/1995 | Stupecky ..................... 439/191 |
| 5,637,006 | A | * | 6/1997 | Almeras ...................... 439/191 |
| 5,641,299 | A | | 6/1997 | Meguro et al. |
| 5,711,558 | A | * | 1/1998 | Woody ........................ 292/335 |
| 5,803,762 | A | * | 9/1998 | Green .......................... 439/347 |
| 5,812,356 | A | | 9/1998 | O'Connor |
| 6,817,879 | B2 | | 11/2004 | Mulvenna et al. |
| 6,851,427 | B1 | | 2/2005 | Nashed |
| 6,943,527 | B2 | * | 9/2005 | Liu et al. ..................... 320/107 |

FOREIGN PATENT DOCUMENTS

| DE | 3238949 A1 | 5/1984 |
| EP | 0 855 299 A2 | 7/1998 |

* cited by examiner

*Primary Examiner*—Phuong K Dinh
(74) *Attorney, Agent, or Firm*—Standley Law Group LLP

(57) ABSTRACT

A combined socket for simultaneously establishing electric as well as hydraulic/pneumatic connections comprising a preferably slot-shaped receiving element in which electric contacts as well as hydraulic/pneumatic ports are integrated and comprising a locking mechanism for locking the positive contact by a plug, the locking mechanism being actuated hydraulically/pneumatically, electrically or electromagnetically.

5 Claims, 3 Drawing Sheets

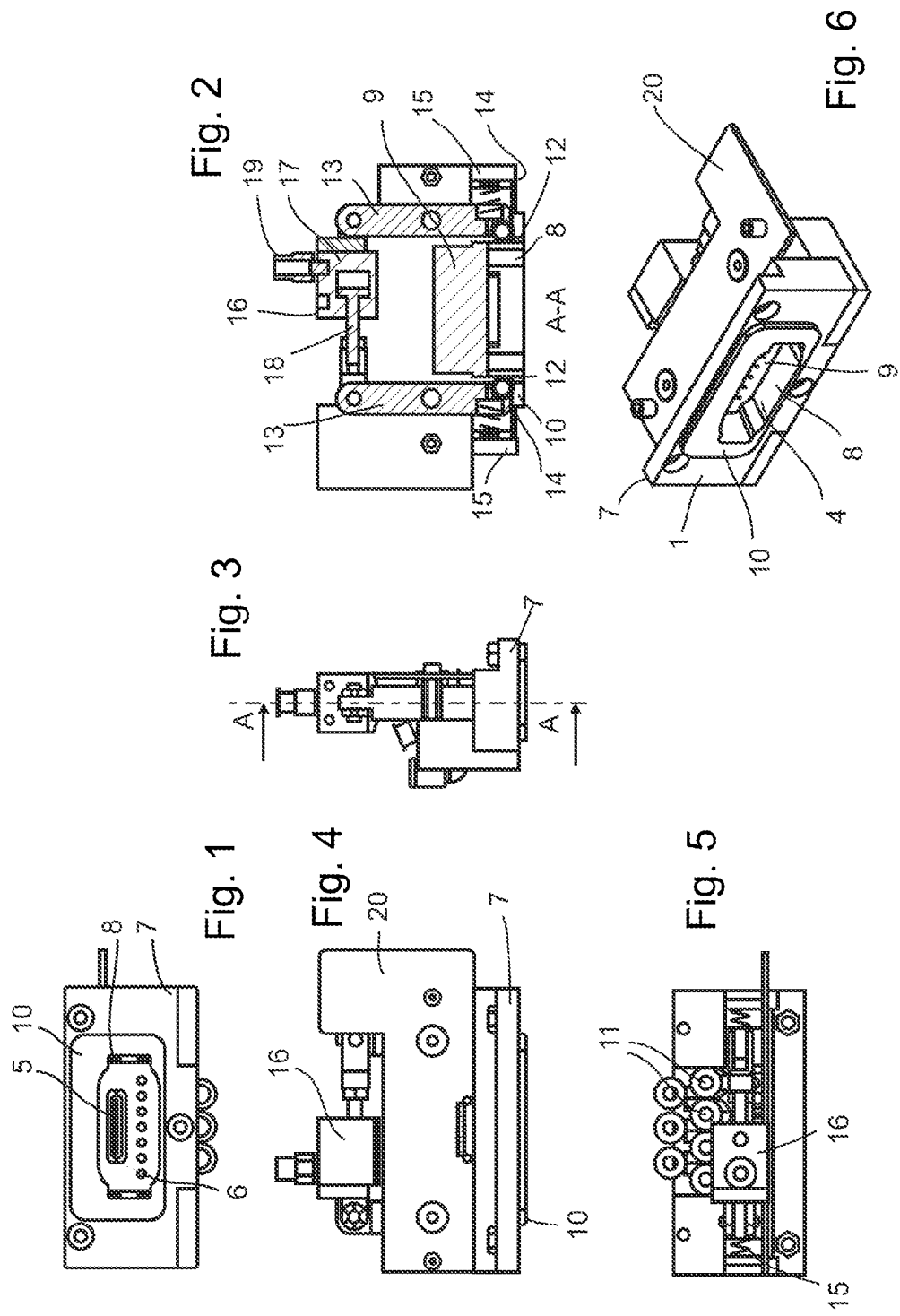

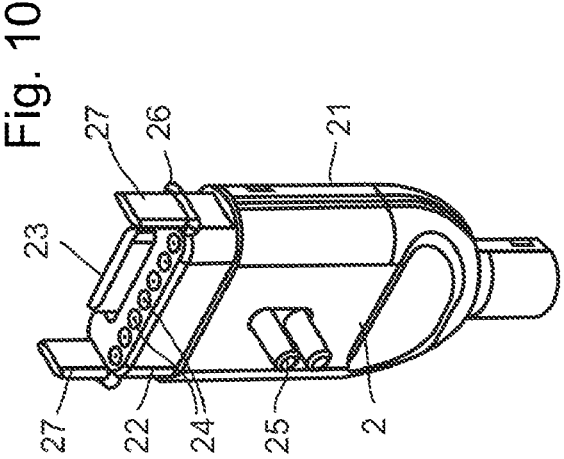
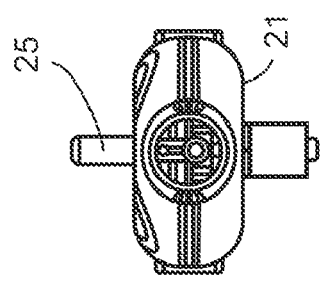
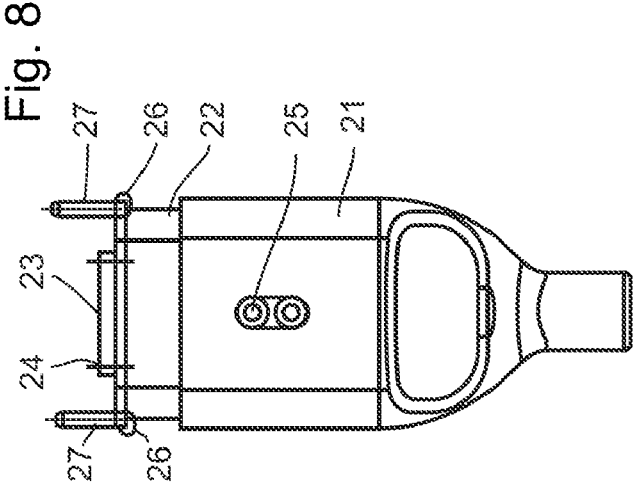
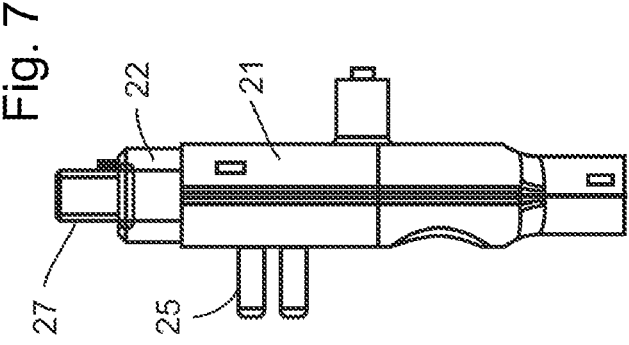

ELECTRIC PLUG DEVICE INCLUDING INTEGRATED HYDRAULIC/PNEUMATIC PORTS

CROSS-REFERENCE TO RELATED APPLICATIONS

This application claims a right of priority under 35 USC §119 from German patent application 10 2007 000 109.8, filed 22 Feb. 2007, the content of which is incorporated by reference as if fully recited herein.

TECHNICAL FIELD

The present invention relates to an electric plug connection comprising integrated hydraulic/pneumatic ports as well as preferably comprising integrated control electronics.

STATE OF THE ART

From the state of the art connector devices for connecting electric or hydraulic/pneumatic apparatuses are known. Electric connector devices usually consist of an electrically insulating plastic casing as well as a number of electric contacts which are preferably accommodated in a receiving chamber open toward an end face in a protected manner. Inside the connector casing electric connecting cables are screwed or soldered with the electric contacts, the connector casing being engaged with the cable in such manner that, in case a mechanical load acts onto the cable, the portions of the cable soldered or screwed with the electric contacts remain as far as possible mechanically unloaded.

Moreover, hydraulic/pneumatic connector devices are known by means of which one or a plurality of pressurized hoses can be connected to pressure consumers. Connector devices of this type usually have stop flanges at which additional sealing rings may be provided as well as screwing means, preferably in the form of sleeve nuts, which are adapted to be operatively engaged with corresponding threads on the side of the pressure consumer or the pressure source so as to establish a pressure-tight contact between the plug and the pressure consumer/pressure source.

It has turned out that generally known plug-in connections of this type are not economical or inapplicable when, for instance, a plurality of hydraulic/pneumatic as well as electric connections are provided at an apparatus and, moreover, the connecting space available is very small.

TECHNICAL PROBLEM

In view of these problems, the object of the present invention is to provide a plug device by which electric as well as hydraulic/pneumatic connections can be established in an as space-saving and economic manner as possible.

TECHNICAL SOLUTION

This object is achieved by a connector device comprising the features of claim 1. Advantageous further developments of the invention are the subject matter of the subclaims.

BRIEF DESCRIPTION OF THE FIGURES OF THE DRAWINGS

The invention will hereinafter be described in detail by way of preferred embodiments with reference to the accompanying drawings, wherein identical parts are identified with identical reference numbers and wherein:

FIG. 1 shows a front view of the socket of the connector device according to the invention in accordance with a preferred embodiment of the invention;

FIG. 2 is a partly cut top view of the socket according to FIG. 1;

FIG. 3 is a side view of the socket in accordance with FIG. 1;

FIG. 4 is a partly cut top view of a socket according to FIG. 1; mounted in a Y-piece of an endoscope, catheter or trocar;

FIG. 5 is a rear view of a plug of the connector device according to the preferred embodiment of the present invention;

FIG. 6 shows a perspective view of the plug according to FIG. 5;

FIG. 7 shows a side view of the plug in accordance with FIG. 5;

FIG. 8 shows a top view of a Y-piece including a mounted socket according to FIG. 1;

FIG. 9 shows a rear view of a Y-piece;

FIG. 10 is a perspective view of a Y-piece; and

BEST WAY TO CARRY OUT THE INVENTION

Figure 11:
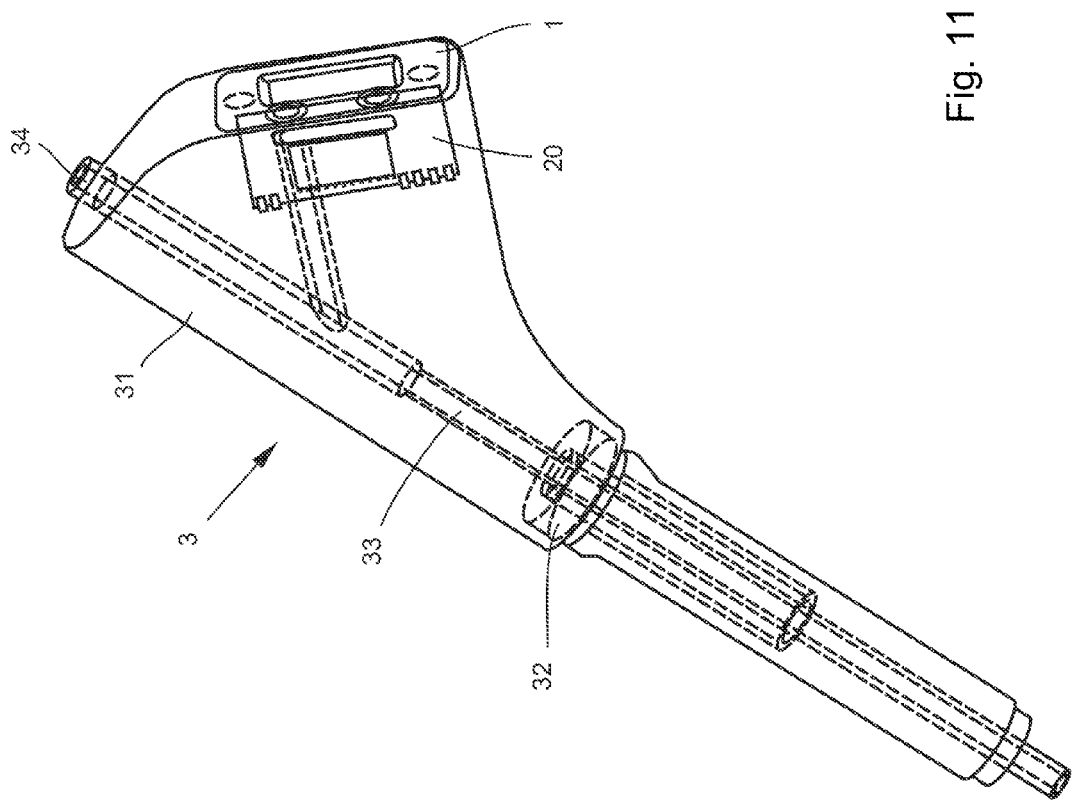
FIG. 11 is a basic perspective view of a Y-piece.

The connector device according to the invention in accordance with a preferred embodiment of the invention comprises a socket 1 as well as a plug 2 especially adapted to the socket. In accordance with the invention, a Y-piece 3 of an endoscope, catheter, trocar or similar medical working instrument is equipped with the socket 1 or the plug 2 according to the preferred embodiment of the invention.

According to the FIGS. 1 and 2, the socket 1 according to the invention is a so-called combined socket for simultaneously establishing electric as well as hydraulic/pneumatic connections. For this purpose, the socket 1 has a contact slot (shaft) 4 in which a number of electric terminals 5 as well as hydraulic and/or pneumatic ports 6 are accommodated. The contact slot 4 is formed of a casing portion of the socket consisting of a front plate 7 at which a substantially rectangular opening is cut out. A sleeve member 8 which is open at a front face is inserted into said opening, whereas, at the opposed rear face, a closing plate 9 including contact terminals embedded therein is disposed. Around the open front face of the sleeve 8 a stop plate 10 is formed integrally with the same, which stop plate is attached to (abuts against) the casing plate 7 in a flange-like manner and thus fixes the sleeve 8.

According to FIG. 1, moreover a number of through-bores which are formed into threaded bores at the rear side of the back plate 9 are formed in the closing or back plate 9. Hydraulic connecting pins 11 to which pressure lines (not shown) can be connected in a fluid-tight manner (e.g. by clamping rings) are screwed into said threaded bores. As an alternative, the connecting pins 11 can also be formed integrally with the back plate 9 or can be welded/soldered to the latter. Preferably the through-bores are surrounded at the front side of the back plate 9 by annular grooves into which sealing rings are glued (not shown).

As is especially shown in FIG. 2, the sleeve 8 inserted in the casing plate 7 includes lateral openings or slits 12 which preferably have a rectangular shape.

On both sides of the sleeve 8 centrally rotatably supported levers 13 each having at the one lever end thereof a clamping roller 14 rotatably supported thereon are arranged at the casing of the socket 1. Furthermore, each lever 13 extending in parallel to the plug-in direction of the sleeve 8 at the side thereof is biased by means of a spring element 15 such that the two opposed clamping rollers 14 are elastically urged/pushed into the lateral openings or slits 12 of the sleeve 8. The opposed other ends of the two clamping levers 13 are coupled to a lever actuating mechanism 16.

In a preferred embodiment of the invention said actuating mechanism 16 consists of a hydraulic/pneumatic cylinder 17 in which a piston having an axial movement restriction is slidingly supported. The cylinder 17 is rotatably hinged to the one clamping lever end, whereas the piston 18 is rotatably hinged to the end of the opposed clamping lever 13. The cylinder 17 further includes a hydraulic/pneumatic port 19 for the actuation thereof.

In this context, it is noted that instead of the cylinder/piston arrangement described by way of example in the foregoing a different type of actuating mechanism can be provided as well. For instance, also an electromotive unit including a transmission (toothed rack, spindle etc.) connected thereto, a piezoelectric element, a directly acting moving coil or alternatively a system of coil and axially movable armature is applicable.

Preferably the socket 1 according to the invention can be equipped with an electronic means 20 fixed thereto in the form of a printed circuit board by which, for instance, control signals for activating/deactivating the actuating means 16 are transmitted.

In accordance with the FIGS. 7 to 10, the plug according to the invention consists of a plug casing 21 preferably made of two plastic shells connected to each other and enclosing at least partially a plug-in element 22 having integrated contact pins 23 and hydraulic ports 24. In the present case, the plug-in element 22 includes a number of sliding contacts or contact pins the shape of which is adapted to the socket-side contacts for an electric positive contact. The position and size of the hydraulic/pneumatic ports 24, too, are adapted to the socket-side ports.

Accordingly, the plug-in element 22 of the plug 2 according to the invention comprises a plurality of longitudinally extending through-bores which are enclosed by annular grooves at the front side of the plug-in elements 22 and which are provided, at the rear side of the plug-in element 22, with connecting means preferably in the form of connecting pins 25 for a tight connection of hydraulic/pneumatic pressure hoses/tubes. In the present embodiment parts of said connecting pins 25 for the hydraulic hoses project at the upper and/or lower side of the plug casing 21 from the latter.

Moreover, the plug-in element 22 has at its front portion at least in the lateral area bead-shaped projections 26 protruding to the side and defining undercuts on both sides in the plug-in direction. Finally in a preferred embodiment the plug-in element 22 is designed to have two spreading straps/tabs 27 (not absolutely necessary, however) which extend in the plug-in direction from the front face of the plug-in element 22 and thus represent an L-shaped extension of the laterally protruding bead-shaped projections 26 in axial direction of the plug-in element 22.

Concerning the mode of operation as well as the attainable advantages of the device according to the invention, the following is stated:

For simultaneously establishing an electric connection as well as hydraulic/pneumatic connections the above described plug 2 according to the invention is inserted into the receiving slot (slot) 4 of the above described socket 1 according to the invention. The contact pins or sliding contacts of the plug come into an electric contact with the contact terminals or sliding contacts of the socket 1, when a predetermined plug-in distance is exceeded.

Furthermore, upon inserting the plug-side plug-in element 22 into the plug-in slot 4 of the socket 1, the two spreading straps/tabs 27 (or, unless provided, the lateral projections 26) of the plug 2 are engaged with the socket-side clamping rollers 14 and force the latter against the spring bias thereof out of the lateral openings 12 of the sleeve 8 forming the plug-in slot 4. In this way, the plug-side plug-in element 22 can be inserted into the socket-side sleeve 8 substantially without a major resistance.

As soon as the hydraulic/pneumatic connecting ports at the end face of the plug-side plug-in element 22 get into contact with the sealing rings on the side of the socket 1, the two clamping rollers 14 are simultaneously positioned on both sides of the plug-in element 22 directly behind the lateral bead-shaped projections 26. As a result the plug 2 is mechanically held in the plug-in slot 4 of the socket 1 by the biasing forces of the two biasing springs 15 acting onto the clamping rollers 14.

In a preferred embodiment of the invention a hydraulic/pneumatic port of the plug-socket connection is in fluid connection with the hydraulic/pneumatic actuating mechanism 16 for the levers 13. When said hydraulic/pneumatic connection is pressurized with a pressure medium by a fluid pressure source (not shown), this pressure medium flows via the plug-socket connection to the hydraulic/pneumatic actuating mechanism 16, whereby the two ends of the clamping levers 13 are pushed away from each other. At the same time the two clamping rollers 14 are pressed via the clamping lever mechanism against the casing 21 of the plug 2 as well as partially in the plug-in direction of the plug 2 against the two laterally protruding bead-shaped projections 26, whereby the hydraulic ports are pressed against each other in a sealing manner.

WAY(S) TO CARRY OUT THE INVENTION

As an alternative to this configuration, it is also possible, however, that in the moment in which by spring-elastic snap-in of the opposed clamping rollers 14 an electric connection between a plug-side contact and a socket-side contact is closed an electric signal is transmitted by the socket-side printed circuit board 20 to the actuating mechanism 16, whereupon the actuating mechanism 16, e.g. in the form of the afore-described piston/cylinder arrangement or an electromotive or piezoelectric drive means, caulks the clamping rollers 14 against the plug casing as well as against the laterally protruding projections 26.

Described more concretely, a sensor in the form of an electrically closing wire bridge, an optical light barrier, a mechanically operable micro switch, a magnetically operable reed relay or Hall sensor or an inductive or capacitive oscillator circuit, for instance, is arranged by which the presence of a plug inside the socket sleeve 8 can be detected, wherein the respective signal sent from the sensor is processed into an activating signal for the actuating mechanism 16.

Further, as an alternative (and in addition, where appropriate) it is also possible to manually activate the actuating mechanism 16 by applying/transmitting an appropriate electric or hydraulic/pneumatic signal, independently of the plug-in operation of the plug 2 into the socket according to the invention.

By means of the connector device according to the invention hydraulic/pneumatic as well as electric connections are established simultaneously upon inserting a plug 2 into a corresponding socket 1. The hydraulic/pneumatic ports as well as the electric terminals are integrated in a common plug-side plug-in element 22. Due to this configuration it is no longer necessary to separately arrange electric and hydraulic/pneumatic ports which require an appropriate minimum space for handling the same.

Moreover, according to the invention it is possible to design the socket 1 to include an electromotive or pneumatic/hydraulic locking means 16 which is preferably automatically actuated upon inserting the plug 2 into the socket and thereby, on the one hand, locks the hydraulic/pneumatic ports in a fluid-tight manner and, on the other hand, prevents the plug 2 from being unintendedly loosened or removed from the socket 1.

It has turned out that especially with mechanical, manually operable locking means, as they are known from prior art, a plug-socket connection cannot or can only be secured with difficulties against unintended loosening in particular when the hydraulic/pneumatic lines are still under pressure, whereas in the present embodiment according to the invention the locking means is activated automatically upon inserting the plug-side plug-in element 22 into the plug-in slot 4 of the socket 1 or upon applying pressure to at least one of the hydraulic/pneumatic lines (according to the principle of a pressure relief valve).

The latter embodiment has the advantage that upon pressure relief of the respective pressure line the locking means 16 is released automatically, whereas those clamping or actuating means 16, which are activated by the inserting operation of the plug 2 into the socket 1 or by an appropriately manually triggered electric or hydraulic/pneumatic signal, can only be manually released again by an appropriate electric or hydraulic/pneumatic counter-signal.

In FIG. 11 a preferred example of application for the connector device according to the invention is shown.

From prior art, especially in the field of medical engineering, it is known to dock, at the proximal end of endoscopes, trocars, catheters and similar minimally invasive working instruments, so-called Y-pieces 3 by which, on the one hand, medical instruments can be actuated to the distal end of the endoscope/trocar, and, on the other hand medical active ingredients, fluids or further medical working instruments can be guided to the distal end of the endoscope/trocar.

Modern instruments of this species have movable distal end pieces which have to be electrically and/or hydraulically/pneumatically actuated. For this purpose, these generic instruments are electrically and/or hydraulically/pneumatically connected to so-called supply stations equipped with actuating means in the form of control desks, for instance.

Since the requirements to hygiene are constantly increasing and at the same time complex cleaning methods become more and more expensive, the need of so-called throw-away devices is constantly increasing. Therefore it is provided to design working instruments of the afore-mentioned species as such a throw-away product which can be connected to the control and supply station via a plug-in supply line.

According to the invention, a Y-piece 3, generally known from prior art, of an endoscope/trocar/catheter or similar medical working instrument comprises the socket 1 according to the invention shown in FIGS. 1 to 6, which socket 1 is integrated in the casing of the Y-piece 3.

Consequently, the Y-piece 3 according to the invention consists of a casing 31 preferably manufactured of plastic material and having a front connection 32 to which an endoscope shaft, trocar or catheter shaft can be connected. Said connection has an internal through-bore 33 extending to a first rear channel opening 34 of the Y-piece 3. The socket 1 according to the invention is arranged below the through-passage 33 formed in the Y-piece 3, wherein a number of hydraulic/pneumatic lines as well as electric connections lead into the through-passage 33 on the side of the Y-piece from the socket.

All substantially lines required for operating the working instrument extend through the shaft into the Y-piece 3 and end there at the electric terminals as well as hydraulic/pneumatic ports of the socket 1 according to the invention. If the present medical working instrument is a throw-away product, for putting into operation it can be connected to the control and supply station (not shown) electrically as well as by fluid via the connector device according to the invention and can be separated from the control and supply station after use thereof by removing the plug 2 according to the invention from the socket 1 according to the invention accommodated in the Y-piece without the control and supply station being contaminated by the working instrument. If also on the side of the control and supply station not shown in detail there is likewise provided a socket 1 according to the invention, also the set of pipes/hoses required for operation and supply, which consequently has a plug according to the invention at both ends, can be separated from the control and supply station in order to be subjected to a cleaning and/or disinfecting operation.

INDUSTRIAL APPLICABILITY

The combined socket and plug, respectively, of the invention can e.g. be used in the field of medicine techniques and preferably in an endoscope device.

What is claimed is:

1. A combined socket for simultaneously establishing electric and hydraulic/pneumatic pressure connections, through electric and pressure lines, with a plug, comprising:
a slot-like receiving element with integrated electric contacts and hydraulic/pneumatic pressure ports and a mechanism for locking a connection with the plug positively,
wherein the locking mechanism is actuated by inserting the plug into the socket and by applying pressure through the plug from at least one of the pressure lines.

2. The combined socket of claim 1, wherein:
the locking mechanism comprises a piston cylinder unit, actuated by pressure to lock the plug-in connection between the combined socket and the plug.

3. The combined socket of claim 1, wherein:
the locking mechanism comprises a lever supported in a pivotable or linearly movable manner in a casing of the combined socket, the lever having, at one end, a hinged actuating means for pivoting or displacing the lever and, at the other end, a pressing member for coming into contact with the plug when inserted.

4. The combined socket of claim 3, wherein:
the actuating means is activated for locking by the insertion of the plug into the combined socket.

5. A Y-piece of a medical working instrument, preferably an endoscope, a trocar or a catheter, comprising:
a combined socket for simultaneously establishing electric and hydraulic/pneumatic pressure connections, through electrical and pressure lines, with a plug, the socket comprising:
a slot-like receiving element with integrated electric contacts and hydraulic/pneumatic pressure ports and a mechanism for locking a connection with the plug positively,
wherein the locking mechanism is actuated by inserting the plug into the socket and by applying pressure through the plug from at least one of the pressure lines.

* * * * *